United States Patent [19]

Knopf et al.

[11] 3,940,542
[45] Feb. 24, 1976

[54] POLYURETHANE HYDROGEL FIBERS AND TAPES AND COMPOSITES WITH NATURAL AND OTHER SYNTHETIC FIBERS OR FILMS

[75] Inventors: Robert John Knopf, St. Albans; Virgil Edison Matthews; Allen Paul Jones, Jr., both of Charleston, all of W. Va.

[73] Assignee: Union Carbide Corporation, New York, N.Y.

[22] Filed: June 18, 1974

[21] Appl. No.: 480,566

[52] U.S. Cl...... 428/364; 260/2.5 AY; 260/2.5 AD; 260/77.5 SP; 264/184; 428/425
[51] Int. Cl.² B32B 27/08; C08G 18/14; B32B 27/40
[58] Field of Search.. 260/2.5 AY, 2.5 AD, 77.5 SP; 428/364; 264/184

[56] References Cited
UNITED STATES PATENTS

| | | | |
|---|---|---|---|
| 3,149,000 | 9/1964 | Beicos | 260/2.5 AD |
| 3,483,015 | 12/1969 | Fukushima et al. | 260/2.5 AY |
| 3,492,154 | 1/1970 | Einstman | 260/2.5 AY |
| 3,562,374 | 2/1971 | Okamoto et al. | 260/2.5 AY |
| 3,666,542 | 5/1972 | Kigane et al. | 260/2.5 AY |
| 3,694,396 | 9/1972 | Nakahara et al. | 260/77.5 SP |
| 3,781,231 | 12/1973 | Janssen et al. | 260/2.5 AD |
| 3,789,027 | 1/1974 | Traeubel et al. | 260/2.5 AG |
| 3,821,136 | 6/1974 | Hudgin et al. | 260/2.5 AD |
| 3,822,238 | 7/1974 | Blair et al. | 260/2.5 AD |

*Primary Examiner*—H. S. Cockeram
*Attorney, Agent, or Firm*—Francis M. Fazio

[57] ABSTRACT

Method for the production of water swellable, lightly crosslinked, hydrogel polymer tapes or fibers comprises extruding an isocyanato terminated prepolymer of a poly(alkyleneoxy) polyol and an organic diisocyanate into a coagulant or crosslinking bath containing water or organic polyamine as the crosslinker.

46 Claims, No Drawings

3,940,542

POLYURETHANE HYDROGEL FIBERS AND TAPES AND COMPOSITES WITH NATURAL AND OTHER SYNTHETIC FIBERS OR FILMS

BACKGROUND OF THE INVENTION

The use of fibrous materials as absorbents for moisture is a well known widespread practice. In this application many of the natural and synthetic fibers have been used and extensive efforts have been made to improve the absorption properties of the materials. One of the major deficiencies of the natural and synthetic materials heretofore used has been the tendency for them to release the absorbed moisture when pressure has been applied to the moisture containing material. The fact that pressure causes the absorbed fluid to be expelled from the fibers is known as reversible absorption. For many applications, however, irreversible absorption is desired, for example, in surgical dressings, diapers, bed pads, catamenials, and the like, whereby the absorbed moisture is retained in the absorbent material under an applied pressure.

Within the past few years recent innovations have resulted in the production of materials having such irreversible absorption properties; these materials are now known as hydrogels. In most instances they have been produced in powder or particulate form and even, in some instances, in film form. However, few if any hydrogel fibers are known to exist. An especially interesting characteristic of the hydrogel polymers is that when in contact with water they absorb it and swell to a certain point and stop and the final swollen polymer is still similar in shape to its initial unswollen shape. Many of the hydrogels have the ability to absorb many times their original weight in water without becoming soggy or deformed. In general, the hydrogels are used in conjunction with other materials as supports. Among the United States patents that have issued in this field are U.S. Pat. Nos. 3,669,103; 3,589,364; 3,694,301; 3,670,731; 3,164,565. This is but an exemplary listing and should not be considered complete.

SUMMARY OF THE INVENTION

Water swellable, lightly crosslinked hydrogel polymer fibers and tapes or ribbons are produced by extruding or spinning a solution of an isocyanato terminated prepolymer comprising the reaction product of a poly(alkyleneoxy) polyol having an average molecular weight up to about 25,000 and an organic diisocyanate into a coagulant bath whereby said prepolymer is lightly crosslinked by a crosslinking agent which is either water or an organic polyamine. The crosslinking agent is present in the coagulant bath at a very dilute concentration.

DESCRIPTION OF THE INVENTION

It was recently discovered that a new class of polyurethane hydrogels could be produced by the formation of an isocyanato terminated prepolymer obtained by the reaction of poly(alkyleneoxy) polyol and organic dissocyanate followed by light crosslinking with water or an organic polyamine in which the amount of crosslinker used is sufficient to produce an essentially water insoluble hydrogel rather than the end-capped product. The manner in which these hydrogels are produced is the subject of another invention but will become apparent hereinafter. Attempts to produce fibers and tapes or ribbons from said hydrogels presented problems in spinning of the final product; as a consequence it was necessary to seek some other method for the production of fibers and tapes of these water insoluble, water swellable, lightly crosslinked hydrogels.

It has now been found that fibers or tapes can be produced by extruding or spinning a solution of an isocyanato terminated prepolymer, which is the reaction product of a poly(alkyleneoxy) polyol having an average molecular weight up to about 25,000 and an organic diisocyanate, into a crosslinking bath that contains a critical quantity of crosslinker; the crosslinker being water or an organic polyamine. As the prepolymer solution enters the bath, the free isocyanato groups react with the crosslinker to produce the hydrogel polymer and in the same operation the prepolymer solvent is removed and an insoluble, lightly crosslinked hydrogel fiber or tape is produced which retains the shape of the extruded stream. Thus, the crosslinking and/or coagulating bath serves two separate and distinct functions, reaction of the isocyanato terminated prepolymer to produce the hydrogel and removal of the prepolymer solvent to permit coagulation. The use of this bath as a means for completing the reaction between the isocyanato terminated prepolymer and the crosslinker in the production of fibers is distinctive since it is not ordinarily used in this manner. The ordinary usage is as a coagulant bath; it has not heretofore, to our knowledge, been used as the means for reacting a component of the molecule with another reactive component that must be present at a critical concentration so as to produce the desired final molecule in fiber or tape form.

The poly(alkyleneoxy) polyols that are used in producing the isocyanato terminated prepolymers are those having a molecular weight up to about 25,000. These polyols can be diols, triols, or tetrols, with the molecular weight of the polyol varying depending upon which is used.

The suitable diols are the poly(ethyleneoxy) glycols which have a molecular weight of from about 4,000 to about 25,000, preferably from about 6,000 to about 20,000. These diols are well known and many are commercially available. Minor amounts, preferably up to about 35 weight percent, of a poly(propyleneoxy) glycol or a poly(butyleneoxy) glycol can also be present. The polyols can be block or random copolymers containing mixtures of ethyleneoxy, propylenoxy, or butyleneoxy units.

The triols and tetrols that can be used are those having a molecular weight of from about 92 to about 5,000, preferably from about 500 to about 1,500. These can be the poly(alkyleneoxy) polyols wherein the alkyleneoxy group contains from 2 to 4 carbon atoms and they can be homopolymers or block or random copolymers having three or four reactive hydroxyl groups. One can also use the aliphatic polyhydroxyl compounds of the formula $C_nH_{2n+2-m}(OH)_m$ wherein n is an integer having a value of from 3 to 6 and m has a value of 3 or 4.

Illustrative of the suitable polyols are poly(ethyleneoxy) diol, poly(propyleneoxy) diol, poly(butyleneoxy)diol copoly(ethyleneoxy-propleneoxy) diol, poly(ethyleneoxy) triol, poly(ethyleneoxy)tetrol, poly(propyleneoxy) triol, copoly(ethyleneoxy-propyleneoxy) triol, copoly(ethyleneoxy-butyleneoxy) triol, glycerine, sorbitol, 1,2,6-hexanetriol, trimethylolpropane, pentaerythritol, dipentaerythritol, and the like.

The alkyleneoxy adducts of the mono or polyamines such as ethylamine, ethanolamine, diethanolamine, ethylenediamine, propylenediamine, isopropanolamine, hexamethylenediamine, and the like mixtures thereof can be used if desired. In addition, one can include some polycaprolactonepolyol or conventional polyester polyol.

The isocyanato terminated prepolymers can be produced by reacting the poly(alkyleneoxy) diol with the organic diisocyanate. In another embodiment, the isocyanato terminated prepolymers can be produced by reacting a mixture of poly(alkyleneoxy) diol and poly(alkyleneoxy)triol and/or tetrol with the organic diisocyanate. When a mixture of polyols is used in producing the hydrogels the mole ratio of the diol to the higher polyols is at least 6:1 and can be as high as about 40:1. Preferably this mole ratio is from about 15:1 to about 30:1, and more preferably from about 20:1 to about 25:1. It has been observed that the mole ratio of diol to higher polyol has an effect on water uptake; the higher the mole ratio, the higher the water uptake.

Any of the known organic diisocyanates can be used in the reaction with the polyol to produce the isocyanato terminated prepolymer. are well known to those skilled in the polyurethane art and illustrative thereof one can mention, tolylene diisocyanate, phenylene diisocyanate, hexamethylene diisocyanate, isophorone diisocyanate, methylene bis(4-phenylisocyanate), 4,4'-methylenebis(0-tolylene isocyanate), dimer acid diisocyanate, 2,2,4-trimethylpentane diisocyanate, aniline-formaldyhyde polyisocyanates having an average of from about 2 to about 3 isocyanato groups per molecule. If desired a small amount of higher functionality polyisocyanates can be present. In producing the isocyanato terminated prepolymer one reacts an excess of the diisocyanate with the polyol. The ratio of isocyanato groups to hydroxyl groups is from about 1.2 to 1.6 equivalents of isocyanato per equivalent of hydroxyl. An equivalent amount of isocyanato sufficient to react with any water present in the reactants can also be added. It has been observed that at the lower ratios the final hydrogel polymer becomes too soluble, while at ratios above 1.6:1 the water uptake of the final hydrogel decreases. In this reaction any of the known catalysts can be used, such as, dibutyltin dilaurate, stannous octoate, triethylenediamine, lead octoate, bis(dimethylamino) ethyl ether, and the like. The catalyst is present at a concentration of from about 0.001 to about one percent by weight. The conventional catalytic amounts are employed.

Production of the isocyanato terminated prepolymer is carried out in the presence of an inert anhydrous organic solvent such as benzene, toluene, trichloroethylene, trichloroethane, bis(2-chloroethyl) ether, methyl ethyl ketone, ethylene dichloride, ethyl acetate, xylene, and the like.

The temperature at which the prepolymer is produced can vary from about 50° C. to about 170° C. and is not critical to the reaction. The time required to carry the reaction to completion will vary depending upon the particular reactants and catalyst used, the size of the batch and other factors known to those skilled in the art. The reaction for the preparation of the prepolymer is preferably carried out under anhydrous conditions and under an inert gas atmosphere.

The isocyanato terminated prepolymer concentration in the spinning solution can vary from about 20 to about 40 weight percent. It will vary depending upon the particular prepolymer, its molecular weight, the solvent, and other factors, as is known to those skilled in the fiber spinning technology. The preferred concentration is one which yields a solution having a proper spinning viscosity, between 20,000 and 150,000 centipoises at the spinning temperature, generally about 40° C to about 50° C. The solution should not be so dilute as to present problems during spinning or so concentrated as to gel on standing before spinning.

In producing the hydrogel fibers the isocyanato terminated prepolymer solution is extruded through a spinnerette, or for tapes as a thin flat stream, into the crosslinking and coagulating bath. This bath contains a solvent in which the solvent of the prepolymer solution is soluble and a crosslinking agent. The coagulant bath solvent can be any inert organic solvent and can be aliphatic or aromatic; the important considerations here are that it is not reactive to the isocyanato group and that the prepolymer solvents are soluble in it. Illustrative of suitable coagulant bath solvents one can mention hexane, heptane, dipropyl ether, naphtha, dibutyl ether, octane, nonane, and the like. The preferred coagulants are the aliphatic hydrocarbons boiling below about 150°C. It is also desirable to add a small quantity of the prepolymer solvent to the coagulant bath.

The crosslinking agent is dissolved in the coagulation bath and reacts with the free isocyanato groups on the prepolymer molecule to join them together and form a crosslinked fiber as the prepolymer solution is extruded or spun into the bath. The concentration of crosslinking agent in the coagulation bath is critical since too high a concentration will lead to a simple endcapping reaction yielding a water soluble polymer rather than the desired hydrogel fiber. On the other hand, if the concentration of the crosslinker in the bath is too low, the product will have free isocyanato groups and the polymer will not be adequately crosslinked; this product will be too soluble in water and will not have adequate hydrogel properties.

The concentration of crosslinking agent in a specific coagulating bath is dependent upon many factors but it is readily determined by a simple preliminary spinning run by one skilled in the art. Thus, it is dependent upon the free isocyanato content of the prepolymer, the concentration of prepolymer in the spinning solution, the number of filaments spun or the size of the tape or ribbon extruded, the rate of spinning, the bath size, the residence time of the fiber in the bath, the temperatures of the spining solution and the bath, plus many other variables that are known to those skilled in the art as having an effect on fiber spinning processes and which such individuals know how to overcome. In the laboratory runs set forth in the attached examples, it was found that a crosslinker concentration of from about 0.000001 N to about 0.05 N will produce water swellable, water insoluble, lightly crosslinked hydrogel fibers or tapes. The preferred crosslinker concentration in the bath is from about 0.0001 N to about 0.001 N. The important feature is the use of a concentration sufficient to lightly crosslink the isocyanato terminated prepolymer as it passes through the bath with a minimum of end-capping. Thus, any concentration sufficient to react with all the terminal isocyanato groups in the prepolymer and effect light crosslinking thereof without effecting excessive end-capping can be used. A desired concentration is one in which the number of equivalents of reactive groups in the crosslinking agent used is equivalent to the number of equivalents of isocyanato groups present in the prepolymer. The term lightly crosslinked hydrogel polymer signifies a hydrogel that contains not more than an average of about one crosslink unit per 50,000 average molecular weight of the hydrogel. Preferably there is an average of about one crosslink unit for each 100,000 to 300,000 hydrogel molecular weight and more preferably about one crosslink unit for each 150,000 to 250,000 hydrogel molecular weight.

The suitable crosslinkers are water or the organic polyamines, such as the primary or secondary diamines or triamines. The polyamines can be any of the known aliphatic or aromatic polyamines such as ethylene diamine, diethylene triamine, propylene diamine, hexamethylene diamine, methylenebis(aniline), tolylene diamine, isophorone diamine, trimethylpentane diamine, aniline-formaldehyde adduct polyamines, and the like.

When the isocyanato terminated prepolymer is obtained by the reaction of poly(alkyleneoxy) diol and organic diisocyante, the preferred crosslinking agent is a mixture of organic diamine and organic triamine. However, when the prepolymer is obtained by the reaction of a mixture of poly(alkyleneoxy) diol and poly(alkyleneoxy) triol and/or tetrol and organic diisocyanate, the preferred crosslinker is water, organic diamine, or a mixture thereof.

The spinning operation can be carried out in the manner known to those skilled in the art using spinnerettes of different hole sizes and containing different numbers of holes. The preferred method is to extrude the solution downward into the coagulant bath to avoid blockage of the holes, then use guides to control the direction through the bath and from the bath. The solid, lightly crosslinked, hydrogel fibers can be conducted over wash rolls to remove solvents and thence to drying rolls. The fibers may be collected as continuous filament, tow or chopped into stable by known means; if desired they can be subjected to a stretching treatment at any stage of the process. The equipment required and its operation in producing fibers and tapes are well known in the art.

The fibers and tapes can be blended with other natural and synthetic fibers, films or tapes to make composite blends. The amount of the hydrogel polymer in such composite can vary from 0.1 weight percent to 99.9 weight percent. This amount is dependent upon the desires of the user and how much water absorbency he wishes to impart to the finished article. Among the other materials that can be used in the blend one can mention cotton, wool, linen, flax, polyamides, polyesters, acrylics, modacrylics, acetates, celluloses, polyolefins, polyurethanes, or blends thereof.

The hydrogel fibers produced by this invention have several advantages over previously produced hydrogel powders and granular particles. They can be accurately placed in woven and non-woven articles when combined with other fibers, and they remain in place during handling and even after swelling during use. The water absorbency of the finished article can be controlled or regulated by selecting the reactants and their relative proportions in producing the isocyanato terminated prepolymer used to manufacture the hydrogel fiber and by regulating the amount of hydrogel fiber used in making the composite. A distinct advantage in our invention is the ability to produce, to our knowledge for the first time, a hydrogel fiber of any desired length or denier. Further, the polyurethane hydrogel fibers produced have been found to possess a high absorption capacity for salt solutions in addition to their high capacity for water. The absorption capacities of the fibers can very from about 5 to about 50 times or more their original weight.

The fibers can be used per se or in blends in diapers, bandages, bed pads, catamenials, facial tissues and paper towels, agricultural uses, filters and a plurality of other articles in which moisture absorbency is desired.

The following examples serve to illustrate the invention. Parts are by weight unless otherwise indicated.

EXAMPLE 1

Two hundred grams of a poly(oxythylene) diol having a molecular weight of about 8,565 and 1.19 grams of a poly(oxyethylene)triol (made by reacting glycerol with ethylene oxide) having a molecular weight of about 1190 were dissolved in 905 grams of thiophene free benzene. About 110 grams of distillate was removed and a 111 gram sample was taken and analyzed for its water content. The polyols/benzene mixture was found to contain 0.0046 percent water. About 793 grams of solution containing 175.4 grams of the polyoxyethylene diol and 1.04 grams of the triol were left in the reactor after the distillation.

To the polyol/benzene mixture there were added 7.28 grams of 98 percent pure methylenebis(4-phenylisocyanate), (an amount giving an isocyanato to hydroxyl equivalent ratio of 1.3 to 1) and 118.5 grams of benzene. The resulting solution was warmed to 35°C and 2 drops of dibutyltin dilaurate were added from a medicine dropper. The solution was heated to reflux and held at a temperature of 79°–80° C for 1¼ hours. Analysis of the kettle contents showed that the isocyanate had completely reacted with the polyols and water; the isocyanate equivalent weight of the isocyanato terminated prepolymer solution produced was found to be 89,500 (theory for complete reaction is 67,000).

About 50 ml of the above isocyanato terminated solution was transferred to a syringe fitted with a long stainless steel needle (No. 15), and the syringe was placed in a Compact Infusion Pump, Model 975 (Harvard Apparatus Company). The pump and needle were elevated at an angle and the tip of the needle was placed under the surface of a 50/50 volume percent n-hexane/benzene mixture in a long, shallow enameled pan. The pan contained 3 liters of the solvent in which was dissolved 0.2 gram of ethylene diamine. The prepolymer solution was slowly extruded using the infusion pump to control the rate. The stream of solution quickly solidified in the bath to produce the lightly crosslinked hydrogel fiber and it was drawn away from the needle and through the bath by hand using glass and wooden rods. The resulting thread was dried overnight at 50° C to remove residual solvent. In this manner, about 1.5 grams of a benzene insoluble, lightly crosslinked, water insoluble, water-swellable, hydrogel fiber was recovered. This thread absorbed 37 times its weight of water after 24 hours immersion in distilled water. During the 24 hour immersion, about 46 percent be weight of the fiber dissolved.

EXAMPLE 2

About 450 grams of the poly(oxyethylene)diol having a molecular weight of about 8,565 and 2.67 grams of the poly(oxyethylene) triol having an average molecular weight of about 1190 were dissolved in 1,156 grams of benzene. The mixture was azeotropically distilled to remove 108 grams of distillate, (until distillate was clear) and a 103 gram sample of the benzene/polyol mixture was analyzed and found to contain 0.0062 percent water by weight. Some 1,303 grams of solution containing 417 grams of the diol, 2.4 grams of triol, and 883 grams of benzene were left in the reactor flask, in which the diol/triol mole ratio was 23.4 to 1.

The solution was heated to 79° C and 17.2 grams of methylenebis(4-phenyl-isocyanate) were added, together with 65 grams of benzene. A 0.09 gram portion of dibutyltin dilaurate was added, and the mixture was maintained at reflux for 1 hour. Analysis indicated that the reaction had not gone to completion, the isocyanate equivalent weight of the solution was 50,500 (theory: 60,300). The Brookfield viscosity of the isocyanato terminated prepolymer solution was measured using a Brookfield LVT viscometer, No. 4 spindle, and found to be 5000 cps. at 55° C and 9,100 cps. at 32° C. Films were cast from the solution on glass plates and cured or crosslinked to produce a hydrogel film, both at 51° C for 30¾ hours in an oven and at room temperature exposed only to atmospheric moisture for 56 hours. The oven cured film had an equilibrium water absorption capacity equal to 26.5 times its weight and contained 6 percent by weight of water soluble material. The room temperature cured film has a water uptake of 29.5 times it weight and contained 6.5 percent by weight of water soluble material.

The isocyanato terminated prepolymer solution remaining after removal of samples for analysis and film casting was transferred to a 900cc jacketed, stainless steel pot connected to a ½ B Zenith metering pump. The pump was connected via flexible stainless steel piping to a spinnerrette containing 50 holes of about 0.07 mm diameter each in its face. The spinnerette was placed in a manner such that its face was turned vertically or downwards into the coagulation bath. Attempts to spin with the spinnerette face on a horizontal plane gave sticking of the solution to the face of the spinnerette as it was extruded.

The coagulation bath contained 3 gallons of n-heptane and it was approximately 0.05 N in ethylene diamine. The pump was operated at 8 revolutions per minute, and 10 psi nitrogen pressure was held on the tank. The prepolyer solution was extruded through the spinnerette vertically downwards into the bath, the multifilament yarn of about 520 denier was taken under a guide roll and out of the bath diagonally upwards, over a roll and taken up by hand. As the prepolymer exited into the bath, it reacted to form lightly crosslinked hydrogel polymers and coagulated to a solid. Some 2 to 3 meters of open, multi-filament hydrogel yarn was collected. The hydrogel filaments did not stick together (i.e., they were open) and were opaque and soft in texture. Immersion of a sample in distilled water for 24 hours resulted in the hydrogel fiber absorbing 35 times its weight of water. Evaporation of the filtrate from the water immersion test showed that 42 percent of the fiber had dissolved in the water. After aging for 12 days at room temperature, exposed to the room light, the fibers still absorbed 32 times their weight of water upon immersion in distilled water for 24 hours. In this example, the prepolymer preparation and spinning were carried out under nitrogen.

EXAMPLE 3

A solution containing 650 grams of a poly(oxyethylene) diol of an average molecular weight of about 8,330, 3.97 grams of the same triol used in Example 1 and 1,400 grams of benzene was distilled to remove 134 grams of distillate. The resulting mixture as assumed to be free of water and 25.67 grams of 98 percent pure methylenebis(4phenylisocyanate) together with 94 grams of dry benzene were added. The mixture was warmed to 78° C and 68 grams of a stock solution made from 1 gram of dibutyltin dilaurate and 999 grams of benzene was added (contained 0.068 gm of catalyst). The solution was heated at reflux for 1.5 hours, under nitrogen, then analyzed. The isocyanate equivalent weight of the solution was found to be 84,000 (theory: 56,000). The solution of the isocyanato terminated prepolymer had a Brookfield viscosity (LVT Viscometer, No. 4 spindle) of 43,200 cps at 46° C. The solids content was approximately 33 percent by weight.

The isocyanato terminated prepolymer solution was transferred from the reaction flask to a 900 cc stainless steel tank under a nitrogen atmosphere. The spinning system used was the same as that described in Example 2 except that a 20 gallon coagulation bath was used. The spinnerette used had 15 holes, each hole having a diameter of 0.13 mm. The filaments were extruded vertically downwards at 42° C. into the coagulation bath, which contained a solution of n-heptane that was $7.5 \times 10^{-5}N$ in ethylene diamine and which was held at a temperature of 42° C. As the prepolymer extrudate entered the bath it coagulated and reacted with the crosslinker to produce a solid, lightly crosslinked hydrogel fiber tow. The fibers were taken over a guide near the bottom of the bath then passed diagonally upwards over a roll which had a dip bath beneath it. Fifteen laps of the hydrogel fibers were placed around the roll, and as they traversed it, they passed through the dip bath. The dip bath contained ½inch of water in the bottom and a top layer of heptane (covering the water) through which the hydrogel fibers on the roll passed. The hydrogel fibers were thus washed with heptane saturated with water. A water/acetone mixture (50/50 weight percent) was added to the dip bath as needed to maintain a constant liquid level. The acetone was used to act as a coupling agent to increase the concentration of water in the heptane layer. The purposes of the wash bath were to remove any residual benzene and amine retained in the fiber as it came from the coagulation bath and to ensure the complete reaction of any residual isocyanato groups in the fiber, using water as a secondary cross-linking reagent. The fibers were conducted from the wash roll to two drying rolls, with several laps of fiber on each roll. The drying rolls were held at 30° C via circulation of tempered water through their interiors. From the drying rolls, the fibers passed to a take-up device and were wound onto a standard fiber package. Two packages of 15-filament yarn were collected as follows:

| Run | Spin Pump rpm | Spin Pump psi | Wash Roll Speed, fpm | Drying Roll Speed fpm | Take-up Speed fpm |
|---|---|---|---|---|---|
| 1 | 13 | 160 | 45 | 85 | 120 |
| 2 | 11 | 220 | 45 | 85 | 120 |

Run 1 contained 105 grams of yarn; Run 2 contained 54 grams of yarn. The hydrogel fibers of Run 1 were 89 percent insoluble in benzene at 25° C, they showed a water absorption capacity 25 times their weight, and a water solubility of 7 weight percent. The hydrogel fibers of Run 2 were 83 percent insoluble in benzene, they showed a water absorption capacity 27 times their weight, a water solubility of 2 weight percent, and absorbed 27 times their weight of 0.3N sodium chloride solution.

The results show that the hydrogel fibers were essentially lightly crosslinked when taken from the drying roll, insoluble in benzene and water, and had the same absorption capacity for water and aqueous salt solutions.

Using a similar isocyanato terminated prepolymer solution and following the spinning procedure similar to that described in Example 3, fibers were spun from a seven hole spinnerette, each hole 0.09 mm, in diameter. In this series the coagulant baths contained 0.05 N, 0.5 N and 1.0N ethylene diamine as the crosslinker. Under these particular small scale spinning conditions, the higher concentration of crosslinker produced endcapped, linear urea-urethane polymers that were completely soluble in water on immersion and agitation for 8 hours. While these laboratory spinning conditions did not produce a hydrogel fiber, it is likely that commercial operations can be carried out with the higher crosslinker concentrations.

EXAMPLE 4

An isocyanato terminated prepolymer was prepared using the same ingredients and the same amounts of each ingredient as was employed in Example 3. After 2 hours of reflux, the isocyanate equivalent weight of the 33 percent solids solution was 77,000 (theory for complete reaction is 56,000). The Brookfield viscosity, as determined with a Brookfield Model LVT viscometer, No. 4 spindle was 33,200 cps. at 51° C., 62,000 at 44° C and 165,000 at 35° C.

The prepolymer solution was transferred to a 900 cc dope tank under a nitrogen atmosphere and heated to 40° C during spinning. The tank was sealed under a positive nitrogen pressure of 30 psi, and samples were spun at 4 different coagulation bath conditions using the same spinning equipment described in Example 3 except that the spinnerette has 7 holes, each 0.09 mm. in diameter, the dip bath under the first roll was omitted, and the drying rolls were not heated but held at ambient temperature.

Run 1 was spun at a Zenith Pump pressure of 500 psi. into a coagulant bath containing wet heptane (water as the crosslinker) at a bath temperature of 38° C. The coagulation roll speed was 45 fpm, the drying roll speed was 80 fpm and the take-up roll speed was 120 fpm.

Run 2 was spun at a Zenith Pump pressure of 300 psi into a heptane coagulant bath at 42° C that was 0,001 N in ethylene diamine. Drying roll speed, however, was 85 fpm.

Run 3 was spun at a Zenith Pump pressure of 520 psi into a heptane coagulant bath at 39° C that was 0.0001 N in ethylene diamine; roll speeds were as in Run 1.

Run 4 was spun at a Zenith Pump pressure of 350 psi into a heptane coagulant bath at 42° C that was 0.005 N in ethylene diamine; roll speeds were as in Run 2.

Portions of the fibers from each run were rolled in distilled water for about 8 hours to determine water uptake and percent solubility.

| Run | Water Absorbency | Water Solubility |
|---|---|---|
| 1 | 29 Fold | 6% |
| 2 | 42 Fold | 46% |
| 3 | 37 Fold | 4% |
| 4 | — | 100% |

The results show that a concentration of 0.0001 N ethylene diamine in the heptane or the use of wet heptane produced good hydrogel fibers of high water absorption and low water solubility. The use of a heptane solution that was 0.001 N in ethylene diamine produced a hydrogel fiber, but it had a higher than desired water solubility, and the use of 0.005 N ethylene diamine in the bath failed to produce a hydrogel under the particular spinning conditions used with this specific composition.

EXAMPLE 5

Two separate isocyanato terminated prepolymer solutions were prepared for spinning using the same ingredients and the same proportions of reactants in each. The basic formulation used 960 gm of a polyoxyethylene diol having a molecular weight of 8330, 5.86 gm of a polyoxyethylene triol having a molecular weight of 1190 (made from glycerol and ethylene oxide), and 2200 grams of thiophene free benzene. After drying the polyols/benzene solution via distillation until the distillate was no longer cloudy, 38.26 gm of methylenebis(4-phenylisocyanate) was added, together with enough benzene so that the final solids content of the mixture would be 32 percent by weight. The resulting solution was heated to reflux and 100 gm of a benzene solution containing 0.1 gm, 100 ppm on the total weight of solids, of dibutyltin dilaurate was added. The isocyanate-polyol reaction was carried out by refluxing for 2 hr., the material remaining in the reactors was weighed, and enough benzene was added to each to replace that lost in reflux in order to bring the solids concentration to 32 percent by weight. The two prepolymer solutions were analyzed for isocyanate content. The isocyanate equivalent weights of the solutions were 115,000 and 108,900 respectively (theory: 57,700).

The isocyanato terminated prepolymer solutions were combined and transferred to a 5-gallon dope pot under a nitrogen atmosphere, and the pot was placed under 40 psi nitrogen pressure. The prepolymer solution was heated by circulating water at 55° C through the jacket of the pot. The solution was circulated through a candle filter (150 mesh stainless steel) to supply 2 dual port spinning pumps (1/2 B Zenith; each supplied 2 spinnerettes). Four spinnerettes, each having 25 holes of 0.10 mm diameter, were immersed in a coagulation bath. The spinning set-up used was similar to that described in Example 3 except for the use of guides to separate the four yarn bundles in the bath. A Teflon rod in the bottom of the bath was used to direct the fiber upwards diagonally to the wash bath. The four bundles were brought together into a single 100 filament tow bundle as they emerged from the bath. The coagulation bath contained heptane which was 0.0001 N in ethylene diamine. The yarn was lapped on the first roll (15 laps) and washed as in Example 3, then taken to 2-drying stretch rolls, thence taken up on a take-up device. Fresh heptane which was 0.0001 N in ethylene diamine was fed at a constant rate to the wash bath and allowed to cascade into the coagulation bath, which overflowed to a waste receptacle. Four packages containing 200–250 grams of hydrogel yarn each were collected. The hydrogel yarn had a denier of about 1880 and was open. The hydrogel yarn had a water absorption capacity equal to 22 times its weight and a water solubility of 15.5 percent by weight.

A hydrogel tape was spun by replacing the spinnerettes and pumps by a single pump which fed the isocyanato terminated prepolymer solution into a ½ inch steel tube flattened on one end to form a slit which was ½ inch wide and had an aperture of approximately 0.04 inch. The slit end of the tube was immersed in the coagulant bath in a manner so that the jet of prepolymer solution extruded vertically downwards. The hydrogel tape was carried under the rod at the bottom of the bath, which contained heptane 0.0001 N in ethylene diamine, thence diagonally upwards onto the wash roll. Three laps of tape were lapped on the washed roll and allowed to pass through the wash bath. The hydrogel tape was taken up on a package by hand.

After drying at room temperature until no odor of benzene or heptane could be detected, the hydrogel tape was about ⅛ inch wide. Upon immersion in water for 8 hours (rolled in bottle) it absorbed 42.8 times its weight and 8.5 percent by weight dissolved in the water.

EXAMPLE 6

An isocyanato terminated prepolymer solution was prepared in the same manner as described in Example 5 except that trichloroethylene solvent was used instead of benzene. A solution containing 700 grams of a poly(oxyethylene) diol of an average molecular weight of about 8468 (hydroxyl number of 13.25), 3.92 grams of a poly(oxyethylene) triol of an average molecular weight of about 1,170 (hydroxyl number of 141.5) and 1,714 grams of trichloroethylene was distilled to azeotropically remove 2.0 grams of water. The mixture was cooled to 56° C and 30.7 grams of methylenebis(4-phenylisocyanate) and 0.2105 gram of dibutyltin dilaurate were added to the kettle contents. The solution was heated at reflux for 2 hours, then the heat was removed and 7 grams of solvent replaced. The resulting solution had a total solids content of 30 percent and an isocyanate equivalent weight of 52,763 with a Brookfield viscosity of 42,500 centipoises at 22° C.

The isocyanato terminated prepolymer solution was transferred to a stainless steel dope tank under a nitrogen atmosphere. The spinning system and equipment used were the same as described in Example 5. Two hydrogel fiber samples were produced using a 60 hole spinnerette, each hole having a diameter of 0.1 mm. The first fiber was extruded at a pot temperature of 48° C. (Fiber 1) and the second fiber at a pot temperature of 34° C. (Fiber 2). The coagulation bath was 0.0001 N ethylene diamine in heptane and was at a temperature of about 35° C. The wash bath was also 0.0001 N ethylene diamine in heptane at 22° C. Twenty-six laps of the hydrogel fiber were placed around the roll dipping into the wash bath; this was turning at a speed of 38 fpm. The drying roll was 22° C.; it had eight laps of the fiber around it and was rotated at a speed of 55 fpm. The stretch roll had five laps of the fiber and rotated at 130 fpm. The fiber take up speed was 150 fpm.

The lightly crosslinked hydrogel fibers produced were white, opaque and had a soft hand. Somewhat slower coagulation tendencies were noted for the trichloroethylene solution of this example compared with the previous examples wherein benzene was used. However, it was found that decreasing the temperature of the coagulation bath increased the rate of coagulation. The fibers were insoluble in trichlorethylene solvent and had the following properties:

| Fiber | Denier | Water Absorbency | Water Solubility |
|---|---|---|---|
| 1 | 173 | 21.53 Fold | 0.42% |
| 2 | 131 | 20.94 Fold | 0.44% |

EXAMPLE 7

An isocyanato terminated prepolymer solution was prepared using the same ingredients, ratio of amounts and procedure as employed in Example 6. After 2 hours of reflux the isocyanate equivalent weight of the solution was 68,072 and the Brookfield viscosity was 45,700 centipoise at 22° C (R.T.) with a total solids content of 30 percent.

The isocyanato terminated prepolymer solution was tranferred to a stainless steel dope tank under a nitrogen atmosphere. The spinning system and equipment used were the same as described in Example 5. Three lightly crosslinked hydrogel fiber samples were produced using the conditions summarized in the following table. They were white, opaque and had a soft hand. They were insoluble in trichloroethylene after crosslinking.

| Fiber Sample | 1 | 2 | 3 |
|---|---|---|---|
| Spinning Conditions | | | |
| Spinnerette, holes (0.1 mm) | 25 | 25 | 40 |
| Dope Pot Temp. °C | 40 | 43 | 42 |
| Dope Pump, rpm. | 10 | 10 | 10 |
| Coagulation Bath | Heptane | Heptane | Heptane |
| Ethylane diamine | 0.0001 N | 0.0001 N | 0.0001 N |
| Temperature (°C) | 34 | 34 | 34 |
| Wash Bath | Heptane | Heptane | Heptane |
| Ethylene diamine | 0.0001 N | 0.0001 N | 0.0001 N |
| Temperature, °C | 22 | 22 | 22 |
| Fiber Laps No. | 7 | 5 | 5 |
| Roll Speed, fpm | 52 | 46 | 50 |
| Drying Roll | | | |
| Temperature, °C | 22 | 22 | 22 |
| Speed, fpm | 60 | 60 | 70 |
| Fiber Laps, No. | 14 | 8 | 10 |
| Stretch Roll | | | |
| Temperature, °C | 22 | 22 | 22 |
| Speed fpm | 95 | 95 | 105 |

-continued

| Fiber Sample | 1 | 2 | 3 |
|---|---|---|---|
| Fiber Laps, No. | 5 | 5 | 5 |
| Fiber Takeup Speed, fpm | 150 | 150 | 150 |
| Water Absorbency, fold | 20.04 | 27.81 | 27.21 |
| Water Solubility, % | 3.46 | 12.70 | 13.68 |
| Denier | 242 | 262 | 232 |

EXAMPLE 8

An isocyanato terminated prepolymer solution was prepared with trichloroethylene solvent using the same procedure, ingredients and ratios as in Example 6, except that the total solids content was 32 weight percent. A viscous prepolymer solution resulted which had an isocyanate equivalent weight of 48,353.

The isocyanato terminated prepolymer solution was transferred to a stainless steel dope tank under a nitrogen atmosphere. The procedure and equipment used were the same as that used in Example 7 to obtain a hydrogel fiber except that the prepolymer solution was extruded via a 0.01 inch by 1.5 inches slit type die and no wash roll was employed. In this manner a lightly crosslinked hydrogel tape was obtained that was white, translucent, smooth, flexible with good dimensional characteristics and had excellent appearance. The tape was insoluble in trichloroethylene. The isocyanate terminated prepolymer was extruded at 30° C into a coagulant bath containing a 0.0001 N ethylene diamine in heptane solution. The dwell time in the bath was 11 seconds and there was produced a lightly crosslinked hydrogel tape. This was dried on a drying roll at 32 fpm at 22° C. The dry hydrogel tape was 0.435 inch wide, 0.006 inch thick, had a water absorbency of 23.45 grams of water per gram of tape, and a water solubility of 5.18 weight percent.

EXAMPLE 9

An isocyanato terminated prepolymer solution was prepared as described in Example 8 except that the total solids content was 30 percent. The resulting prepolymer solution had an isocyanate equivalent weight of 45,426 and a Brookfield viscosity of 47,500 centipoises at 22° C. This solution was stored for a period of 20 days during which time the Brookfield viscosity increased to 600,000 centipoises.

The stored isocyanato terminated prepolymer solution was transferred to a stainless steel dope tank under a nitrogen atmosphere. The equipment and procedure used were the same as described in Example 8 except that a conveyor belt was employed in the coagulating bath to support the tape, naphtha was used instead of heptane as coagulant, and the slit type die was positioned about 2 inches above the bath surface extruding the prepolymer first into air thence onto the conveyor belt. Continuous lightly crosslinked hydrogel tape was produced using a slit die 0.007 inch by 3 inches. The isocyanato terminated prepolymer solution was extruded at 80° C into a 95/5 naptha/trichloroethylene coagulation bath that was 0.0001 N in ethylene diamine and that was kept at 23° C. The tape was conveyed through the coagulation bath at a speed of 8 fpm for a 37 seconds dwelling time and then dried at 23° C. The lightly crosslinked, hydrogel tape was smooth, flexible, white, and translucent. It had good dimensional characteristics, being 0.687 inch wide and 0.006 inch thick. It had an excellent appearance and was not soluble in trichloroethylene. Its water absorbency was 32.1 fold and 31.1 percent was water soluble.

What is claimed is:

1. An article of manufacture comprising a composite of (I) a tape or fiber of a water swellable, lightly crosslinked, hydrogel polymer of the isocyanato terminated prepolymer comprising the reaction product of:
   i. a poly(alkyleneoxy) polyol having an average molecular weight up to about 25,000 wherein the alkyleneoxy group contains from 2 to 4 carbon atoms, and
   ii. an organic diisocyanate, said prepolymer lightly crosslinked with an equivalent amount of a crosslinking agent of the group:
   iii. water or organic polyamine; wherein said poly(alkyleneoxy) polyol is a mixture of a major amount of a poly(ethyleneoxy) diol having an average molecular weight of from about 4,000 to about 25,000 and a minor amount of a higher polyol of the group poly(alkyleneoxy) triol or poly(alkyleneoxy) tetrol or aliphatic polyhydroxyl compound of the formula $C_nH_{2n+2-m}(OH)_m$ wherein n has a value of 3 to 6 and m has a value of 3 to 4 or mixtures thereof, said triol or tetrol having an average molecular weight of from about 92 to 5,000 wherein the mole ratio of diol to higher polyol in said mixture is from about 6:1 to 40:1; wherein the equivalents ratio of isocyanato groups to hydroxyl groups is from about 1.2:1 to about 1.6:1; wherein the organic polyamine is a primary or secondary diamine or triamine and wherein the equivalents of reactive crosslinking groups in said crosslinking agent used in equivalent to the number of equivalents of isocyanato groups present in said prepolymer; in combination with (II) a natural or a different synthetic fiber or film.

2. A method for producing a lightly crosslinked, water swellable, hydrogel polymer tape or fiber which comprises the steps of:
   A. producing an organic solvent solution of an isocyanato terminated prepolymer comprising the reaction product of:
      i. poly(alkyleneoxy) polyol having an average molecular weight up to about 25,000, wherein the alkyleneoxy group contains from 2 to 4 carbon atoms, and ii. organic diisocyanate, wherein said poly(alkyleneoxy) polyol is a mixture of a major amount of a poly(ethyleneoxy) diol having an average molecular weight of from about 4,000 to about 25,000 and a minor amount of a higher polyol of the group poly(alkyleneoxy) triol or poly(alkyleneoxy) tetrol or aliphatic polyhydroxyl compound of the formula $C_nH_{2n+2-m}(OH)_m$ wherein n has a value of 3 to 6 and m has a value of 3 to 4 or mixtures thereof, said triol or tetrol having an average molecular weight of from about 92 to 5,000, wherein the mole ratio of diol to higher polyol in said mixture is from about 6:1 to 40:1; and wherein the equivalents ratio of isocyanato groups to hydroxyl groups is from about 1.2:1 to about 1.6:1;

B. extruding or spinning said isocyanato terminated prepolymer solution into a crosslinking bath comprising:
i. a crosslinking agent for the isocyanato terminated prepolymer of the group (a) water or (b) organic polyamine, wherein said polyamine is a primary or secondary diamine or triamine and wherein the equivalents of reactive crosslinking groups in said crosslinking agent used is equivalent to the number of equivalents of isocyanato groups present in said prepolymer; and C. recovering the lightly crosslinked, water swellable, hydrogel tape or fiber.

3. The method for producing water swellable, lightly crosslinked, hydrogel polymer tape or film as claimed in claim 1, wherein said poly(alkyleneoxy) polyol is poly(ethyleneoxy) diol having an average molecular weight of from 4,000 to 25,000.

4. The method for producing water swellable, lightly crosslinked, hydrogel polymer tape or film as claimed in claim 2, wherein said poly(alkyleneoxy) polyol is poly(ethyleneoxy) diol having an average molecular weight of from about 6,000 to 20,000.

5. The method for producing water swellable, lightly crosslinked, hydrogel polymer tape or film as claimed in claim 2, wherein said poly(alkyleneoxy) polyol is a mixture of poly(ethyleneoxy) diol having an average molecular weight of from about 6,000 to 20,000 and a poly(ethyleneoxy) triol having an average molecular weight of from about 500 to 1,500, wherein the mole ratio of diol to triol is from about 15:1 to about 30:1.

6. The method for producing water swellable, lightly crosslinked, hydrogel polymer tape or film as claimed in claim 2, wherein said organic diisocyanate is tolylene diisocyanate.

7. The method for producing water swellble, lightly crosslinked, hydrogel polymer tape or film as claimed in claim 3, wherein said organic diisocyanate is tolylene diisocyanate.

8. The method for producing water swellable, lightly crosslinked, hydrogel polymer tape or film as claimed in claim 4, wherein said organic diisocyanate is tolylene diisocyanate.

9. The method for producing water swellable, lightly crosslinked, hydrogel polymer tape or film as claimed in claim 5, wherein said organic diisocyanate is tolylene diisocyanate.

10. The method for producing water swellable, lightly crosslinked, hydrogel polymer tape or film as claimed in claim 2, wherein said organic diisocyanate it methylenebis(4-phenylisocyanate).

11. The method for producing water swellable, lightly crosslinked, hydrogel polymer tape or film as claimed in claim 3, wherein said organic diisocyanate is methylenebis(4-phenylisocyanate).

12. The method for producing water swellable, lightly crosslinked, hydrogel polymer tape or film as claimed in claim 4, wherein said organic diisocyanate is methylenebis(4-phenylisocyanate).

13. The method for producing water swellable, lightly crosslinked, hydrogel polymer tape or film as claimed in claim 5, wherein said orgnaic diisocyanate is methylenebis(4-phenylisocyanate).

14. The method for producing water swellable, lightly crosslinked, hydrogel polymer tape or film as claimed in claim 2, wherein said crosslinking agent is water present in said coagulant bath at a concentration up to 0.05 N.

15. The method for producing water swellable, lightly crosslinked, hydrogel polymer tape or film as claimed in claim 5, wherein said crosslinking agent is water present in said coagulant bath at a concentration up to 0.05 N.

16. The method for producing water swellable, lightly crosslinked, hydrogel polymer tape or film as claimed in claim 6, wherein said crosslinking agent is water present in said coagulant bath at a concentration up to 0.05 N.

17. The method for producing water swellable, lightly crosslinked, hydrogel polymer tape or film as claimed in claim 9, wherein said crosslinking agent is water present in said coagulant bath at a concentration up to 0.05 N.

18. The method for producing water swellable, lightly crosslinked, hydrogel polymer tape or film as claimed in claim 10, wherein said crosslinking agent is water present in said coagulant bath at a concentration up to 0.05 N.

19. The method for producing water swellable, lightly crosslinked, hydrogel polymer tape or film as claimed in claim 13, wherein said crosslinking agent is water present in said coagulant bath at a concentration up to 0.05 N.

20. The method for producing water swellable, lightly crosslinked, hydrogel polymer tape or film as claimed in claim 2, wherein said crosslinking agent is an organic diamine present in said coagulant bath at a concentration up to 0.05 N.

21. The method for producing water swellable, lightly crosslinked, hydrogel polymer tape or film as claimed in claim 2, wherein said crosslinking agent is ethylene diamine present in said coagulant bath at a concentration up to 0.05 N.

22. The method for producing water swellable, lightly crosslinked, hydrogel polymer tape or film as claimed in claim 5, wherein said crosslinking agent is ethylene diamine present in said coagulant bath at a concentration up to 0.05 N.

23. The method for producing water swellable, lightly crosslinked, hydrogel polymer tape or film as claimed in claim 6, wherein said crosslinking agent is ethylene diamine present in said coagulant bath at a concentration up to 0.05 N.

24. The method for producing water swellable, lightly crosslinked, hydrogel polymer tape or film as claimed in claim 9, wherein said crosslinking agent is ethylene diamine present in said coagulant bath at a concentration of up to 0.05 N.

25. The method for producing water swellable, lightly crosslinked, hydrogel polymer tape or film as claimed in claim 10, wherein said crosslinking agent is ethylene diamine present in said coagulant bath at a concentration up to 0.05 N.

26. The method for producing water swellable, lightly crosslinked, hydrogel polymer tape or film as claimed in claim 11, wherein said crosslinking agent is ethylene diamine present in said coagulant bath at a concentration up to 0.05 N.

27. The method for producing water swellable, lightly crosslinked, hydrogel polymer tape or film as claimed in claim 2 wherein said crosslinking agent is a mixture of organic diamine and organic triamine present in said coagulant bath at a concentration up to 0.05

28. The method for producing water swellable, lightly crosslinked, hydrogel polymer tape or film as claimed in claim 3, wherein said crosslinking agent is a mixture of organic diamine and organic triamine present is said coagulant bath at a concentration up to 0.05 N.

29. The method for producing water swellable, lightly crosslinked, hydrogel polymer tape or film as claimed in claim 4, wherein said crosslinking agent is a mixture of organic diamine and organic triamine present in said coagulant bath at a concentration up to 0.05 N.

30. The method for producing water swellable, lightly crosslinked, hydrogel polymer tape or film as claimed in claim 7, wherein said crosslinking agent is a mixture of organic diamine and organic triamine present in said coagulant at a concentration up to 0.05 N.

31. The method for producing water swellable, lightly crosslinked, hydrogel polymer tape or film as claimed in claim 8, wherein said crosslinking agent is a mixture of organic diamine and organic triamine present in said coagulant bath at a concentration up to 0.05 N.

32. The method for producing water swellable, lightly crosslinked, hydrogel polymer tape or film as claimed in claim 11, wherein said crosslinking agent is a mixture of organic diamine and organic triamine present in said coagulant bath at a concentration up to 0.05 N.

33. The method for producing water swellable, lightly crosslinked, hydrogel polymer tape or film as claimed in claim 12, wherein said crosslinking agent is a mixture of organic diamine and organic triamine present in said coagulant bath at a concentration up to 0.05 N.

34. The method for producing water swellable, lightly crosslinked, hydrogel polymer tape or film as claimed in claim 2, wherein the crosslinking agent is a mixture of ethylene diamine and diethylene triamine present in said coagulant bath at a concentration up to 0.05 N.

35. The method for producing water swellable, lightly crosslinked, hydrogel polymer tape or film as claimed in claim 3, wherein the crosslinking agent is a mixture of ethylene diamine and diethylene triamine present in said coagulant bath at a concentration up to 0.05 N.

36. The method for producing water swellable, lightly crosslinked, hydrogel polymer tape or film as claimed in claim 4, wherein the crosslinking agent is a mixture of ethylene diamine and diethylene triamine present in said coagulant bath at a concentration up to 0.05N.

37. The method for producing water swellable, lightly crosslinked, hydrogel polymer tape or film as claimed in claim 7, wherein the crosslinking agent is a mixture of ethylene diamine and diethylene triamine present in said coagulant bath at a concentration up to 0.05 N.

38. The method for producing water swellable, lightly crosslinked, hydrogel polymer tape or film as claimed in claim 8, wherein the crosslinking agent is a mixture of ethylene diamine and diethylene triamine present in said coagulant bath at a concentration up to 0.05 N.

39. The method for producing water swellable, lightly crosslinked, hydrogel polymer tape or film as claimed in claim 11, wherein the crosslinking agent is a mixture of ethylene diamine and diethylene triamine present in said coagulant bath at a concentration up to 0.05 N.

40. The method for producing water swellable, lightly crosslinked, hydrogel polymer tape or film as claimed in claim 12, wherein the crosslinking agent is a mixture of ethylene diamine and diethylene triamine present in said coagulant bath at a concentration up to 0.05N.

41. The method for producing water swellable, lightly crosslinked, hydrogel polymer tape or film as claimed in claim 2, wherein said poly(alkyleneoxy) polyol is poly(ethyleneoxy) diol, said organic diisocyanate is tolylene diisocyanate, and said crosslinker is a mixture of ethylene diamine and diethylene triamine present in said coagulant bath at a concentration up to 0.05 N.

42. The method for producing water swellable, lightly crosslinked, hydrogel polymer tape or film as claimed in claim 2, wherein said poly(alkyleneoxy) polyol is poly(ethyleneoxy) diol, said organic diisocyanate is methylene bis(4-phenylisocyanate), and said crosslinker is a mixture of ethylene diamine and diethylene triamine present in said coagulant bath at a concentration up to 0.05 N.

43. The method for producing water swellable, lightly crosslinked, hydrogel polymer tape or film as claimed in claim 2, wherein said poly(alkyleneoxy) polyol is a mixture of poly(ethyleneoxy) diol and poly(ethyleneoxy) triol, said organic diisocyanate is tolylene diisocyanate, and said crosslinker is water present in said coagulant bath at a concentration up to 0.05 N.

44. The method for producing water swellable, lightly crosslinked, hydrogel polymer tape or film as claimed in claim 2, wherein said poly(alkyleneoxy) polyol is a mixture of poly(ethyleneoxy) diol and poly(ethylenoxy) triol, said organic diisocyanate is methylenebis(4-phenylisocyanate), and said crosslinker is water present in said coagulant bath at a concentration up to 0.05 N.

45. The method for producing water swellable, lightly crosslinked, hydrogel polymer tape or film as claimed in claim 2, wherein said poly(alkyleneoxy) polyol is a mixture of poly(ethyleneoxy) diol and poly(ethyleneoxy) triol, said organic diisocyanate is tolylene diisocyanate, and said crosslinker is ethylene diamine present in said coagulant bath at a concentration up to 0.05 N.

46. The method for producing water swellable, lightly crosslinked, hydrogel polymer tape or film as claimed in claim 2, wherein said poly(alkyleneoxy) polyol is a mixture of poly(ethyleneoxy) diol and poly(ethyleneoxy) triol, said organic diisocyanate is methylene bis(4-phenylisocyanate), and said crosslinker is ethylene diamine present in said coagulant bath at a concentration up to 0.05 N.

* * * * *

UNITED STATES PATENT OFFICE
CERTIFICATE OF CORRECTION

Patent No. 3,940,542  Dated February 24, 1976

Inventor(s) R. J. Knopf et al

It is certified that error appears in the above-identified patent and that said Letters Patent are hereby corrected as shown below:

Column 3, line 25, should read

--isocyanato terminated prepolymer. These isocyanates are well known to--

Column 5, line 39, "stable" should read

--staple--

Signed and Sealed this eleventh Day of May 1976

[SEAL]

Attest:

RUTH C. MASON
Attesting Officer

C. MARSHALL DANN
Commissioner of Patents and Trademarks